United States Patent [19]

Numazawa et al.

[11] Patent Number: 4,598,697
[45] Date of Patent: Jul. 8, 1986

[54] BLOOD PUMP APPARATUS

[75] Inventors: Masaaki Numazawa, Kamakura; Hidetaka Tashiro, Hatano, both of Japan

[73] Assignee: Senko Medical Instrument Mfg. Co., Ltd., Tokyo, Japan

[21] Appl. No.: 659,095

[22] Filed: Oct. 9, 1984

[30] Foreign Application Priority Data

Dec. 29, 1983 [JP] Japan .................................. 58-247623

[51] Int. Cl.⁴ .............................................. A61M 1/00
[52] U.S. Cl. .......................................... 128/1 D; 604/4
[58] Field of Search .................. 128/1 D; 604/4, 5, 6, 604/7; 3/1.7

[56] References Cited

U.S. PATENT DOCUMENTS

| | | | |
|---|---|---|---|
| 3,791,374 | 2/1974 | Guarino | 128/1 D |
| 4,135,496 | 1/1979 | Chazov et al. | 128/1 D |
| 4,192,293 | 3/1980 | Asrican | 128/1 D |
| 4,459,977 | 7/1984 | Picon et al. | 128/1 D |
| 4,466,804 | 8/1984 | Hino | 604/4 |

*Primary Examiner*—Edward M. Coven
*Attorney, Agent, or Firm*—Hoffmann, Dilworth, Barrese & Baron

[57] ABSTRACT

There is provided a blood pump apparatus which can supply a pulsating flow of the blood to a body of a patient at a desired rate of flow. R waves are detected from an output of an electrocardiograph to produce a timing signal which is used for controlling timing of intermittent actuation of a motor of a blood pump such as a roller-type pump. A rotation speed of the motor required to obtain the desired flow rate of the blood is automatically calculated in accordance with data inputted by an operator, the data including discharge of the pump per a predetermined revolution of the motor, delay time to be lapsed before an actuation of the motor, duration of the actuation of the motor, and amount of the blood to be fed per a unit period of time. The motor is then controlled to rotate at the calculated speed at the intervals synchronized with the detected R waves. The rotation speed of the motor can be controlled accurately by correcting the calculated rotation speed of the motor in accordance with a detected number of revolution of the motor. The timing of each actuation of the motor can also be controlled so that the pump is driven at intervals synchronized with timing signals generated by a pulse generator.

4 Claims, 6 Drawing Figures

BLOOD PUMP APPARATUS

BACKGROUND OF THE INVENTION

1. Field of the Invention

This invention relates to a blood pump apparatus for use in an extracorporeal blood circulation system.

2. Prior Art

Extracorporeal circulation systems are used for circulating the blood of a patient through a treatment device such as an artificial lung or an oxygenator. In such a system, the treated blood is returned to the body of the patient by a blood pump apparatus. And it is a common practice in the art to use as such a blood pump apparatus a blood pump of the type that feeds the blood in a flexible tube by squeezing the tube by one or more rollers, although other types of blood pumps such as a reciprocal type and a diaphragm-type are also known in the art.

Generally, when it is required to use an auxiliary blood pump, an amount of flow of the blood required to be supplied into the body of the patient per a unit period of time is first determined in accordance with the condition of the patient, and then the speed of the pump is set to such a value that the required amount of flow of the blood (ml/min) is obtained. In this case, it is considered desirable that the blood is pumped not in a continuous manner but in a pulsatile manner as is done by the heart.

For this reason, when a conventional roller-type blood pump is used to produce a pulsating flow of the blood, the rotation speed of the pump is previously set to such a value that a desired flow rate of the blood is obtained, and then the pump is controlled to operate intermittently by means of a switch circuit to produce a pulsating flow of the blood. In this case, the switch circuit is so arranged that it closes to begin to operate the pump a predetermined period of time (hereinafter referred to as delay time) after each of R waves of electrocardiogram of the patient is detected, and that it continues to close for a predetermined percentage of time length of the interval between two adjacent R waves (the interval is hereinafter referred to as R-R interval). The reason why the closures of the switch are so determined is as follows:

As shown in FIG. 1, an electrocardiographic wave Wh includes peaks called P, Q, R, S and T waves, and wherein the P wave indicates the excitation of the atria; Q, R and S waves the process of excitation of the ventricles; and T wave the calming down process of the excitation of the ventricles. Peak of the pressure Wv of the interior of the left ventricle appears during the process indicated by the Q, R and S waves when the heart contracts to pump the blood into the aorta. More specifically, the peak of the pressure Wv appears before the T wave but slightly after the S wave. The aortic valve closes during the period A shown in the same figure, which comes after the T wave, when the pressure of the interior of the left ventricle abruptly decreases. And if the blood is subjected to a pressure by the pump before the closure of the aortic valve, the pressure is transferred via the aortic valve to the left ventricle, so that the heart is subjected to an unnecessary and dangerous load.

Accordingly, in the case where such a roller-type blood pump as described above is used for pumping blood into the body of a patient, the aortic valve must have been closed before the pressure of the pumped blood reaches the aorta. This is the reason why the aforementioned delay time should be provided. And if the pump is operated to rotate in such a manner that the blood pressure is increased after the aortic valve has been closed, a sufficient blood pressure can be applied to the proximal portion of the aorta (the portion of the aorta near the aortic valve). This causes the blood to be forcibly introduced into the coronary arteries, which opens to the proximal portion of the aorta at its proximal end to supply the blood to the cardiac muscle, so that a diastolic augmentation can be attained. Incidentally, the R—R interval is a specific value to each patient and is constant, and therefore the duration of each continuous rotation of the pump required to feed an appropriate amount of blood can be determined as a certain percentage of time length of the R—R interval.

The conventional roller-type blood pump described above is so constructed that the rotation speed and the interval, delay time and duration of each operation of the pump are adjusted to desired values manually and independently from each other. And therefore, when using the conventional roller-type pump, the operator has to first adjust the rotation speed of the pump to a selected value at which a desired flow rate of the blood will be obtained and then has to adjust in accordance with the R-waves the timings of the switch circuit so that the desired interval, delay time and duration of each operation of the pump are obtained. Thereafter, the operator further has to readjust the rotation speed of the pump so that the desired flow rate of the blood is obtained, since the flow rate of the blood has been varied by the adjustment of duration of operation of the pump. And in the case where the desired flow rate of the blood and the desired operation timings of the pump have not accurately been obtained by the above adjustment procedure or the condition of the patient has been changed, the operator has to carry out the above procedure again.

Thus the conventional roller-type blood pump requires a very complicated adjustment procedure, however, it is very dangerous and sometimes impossible to carry out such a complicated adjustment during an operation.

SUMMARY OF THE INVENTION

It is therefore an object of the present invention to provide a blood pump apparatus which can feed a pulsating flow of the blood at a desired flow rate and intervals but is free from a complicated manual adjustment of the rotation speed and operation timings of a blood pump.

It is another object of the invention to provide such a blood pump apparatus in which an accurate flow rate control of the blood can be achieved.

Other features and advantages of the invention will appear more clearly from the following description of the preferred embodiments thereof, which description is made with reference to accompanied drawings.

According to the present invention, there is provided a blood pump apparatus for supplying a pulsating flow of blood into a body of a patient in synchronism with an output of an electrocardiograph connectable to the body of the patient comprising a fluid pump driven by a variable rotation speed electric motor for feeding the blood; a data input circuit for inputting data relating to operation of said pump, said data including data representative of discharge of said pump per a predetermined number of revolution of said motor, data representative of delay time to be lapsed before an actuation of said motor, data representative of duration of the actuation of said motor, and data representative of amount of the blood to be fed per a unit period of time; an R-wave detection circuit responsive to the output of the electrocardiograph for detecting R waves therefrom to output a signal indicative of timing of said R waves and data representative of interval between two adjacent ones of said R waves; a calculation circuit for calculating, in accordance with the data representative of said discharge of the pump, said duration of the actuation of said motor, said amount of blood to be fed per a unit period of time and said interval between the two adjacent R waves, a rotation speed of said motor required to feed said amount of blood, said calculation circuit outputting a signal representative of said calculated rotation speed and said duration of the actuation of said motor; a motor drive circuit responsive to said signal indicative of said interval of the R waves and said signal representative of said calculated rotation speed and duration of the actuation of said motor for driving said motor so that said motor begins to rotate at said calculated rotation speed when said delay time has lapsed from each of the detections of said R waves and stops when said duration has lapsed.

The blood pump apparatus can be modified as to further comprise a pulse generator for generating pulse signals similar in timing to said R waves, and a switch circuit for selectively supplying one of the output of the electrocardiograph and said pulse signals outputted from said pulse generator to said R-wave detection circuit.

The blood pump apparatus can be further modified as to comprise a detection device for detecting number of revolution of said motor, said calculation circuit correcting said calculated rotation speed of said motor in accordance with an output of said detection device.

DESCRIPTION OF THE PREFERRED EMBODIMENTS OF THE INVENTION

Figure 1:
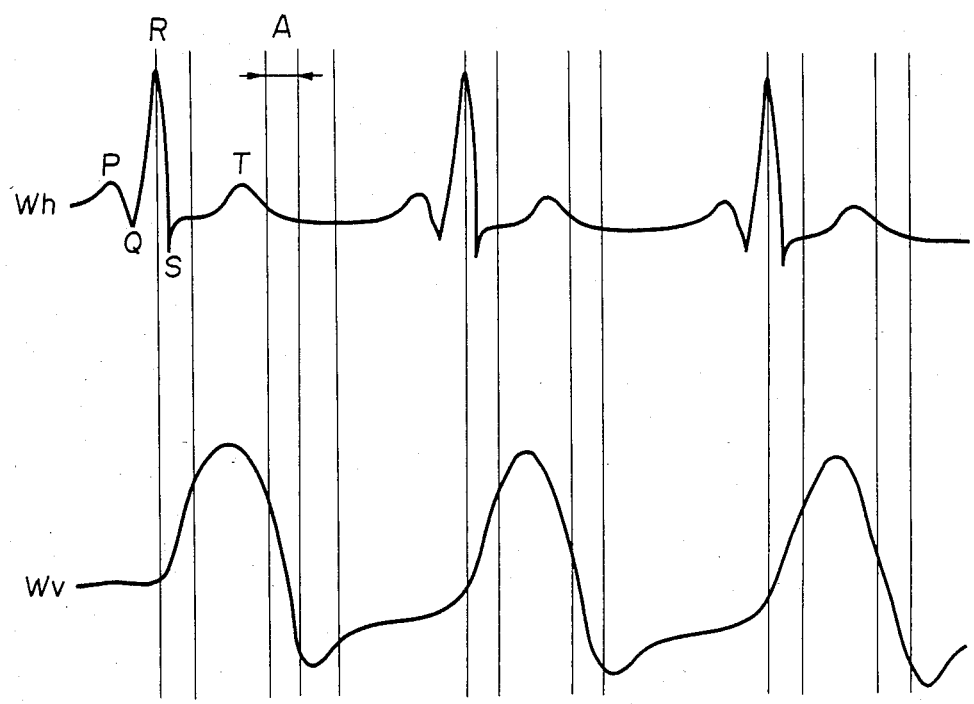
FIG. 1 is an illustration showing waveforms of an output of an electrocardiograph and pressure at the interior of a left ventricle of a heart.
Figure 2:
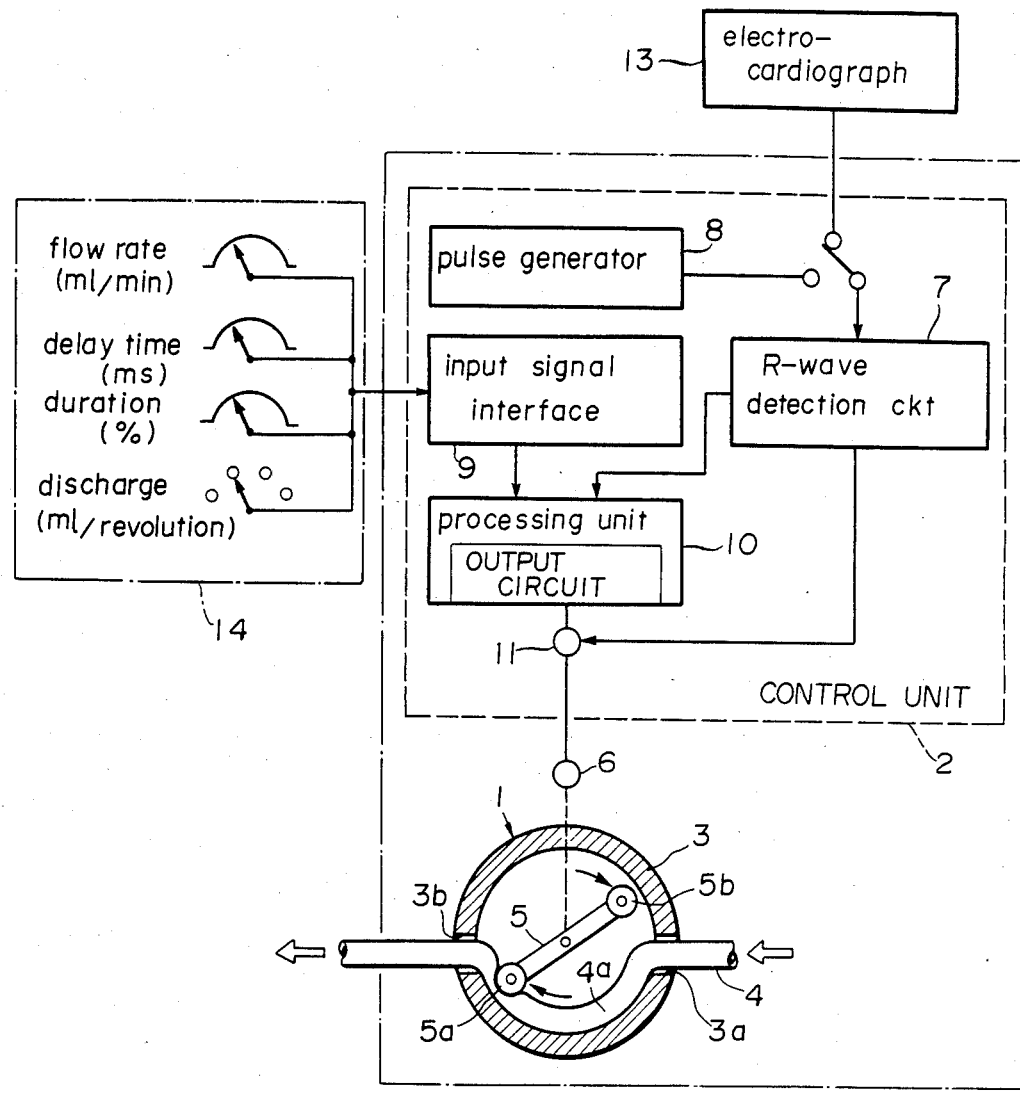
FIG. 2 is a block diagram of a blood pump apparatus provided in accordance with the present invention.

FIG. 2 shows an apparatus provided in accordance with the present invention. This apparatus comprises a roller-type blood pump 1 and a control unit 2 for controlling the pump 1 to operate at desired speed and intervals. The pump 1 comprises a cylindrical housing 3, a flexible tube 4 through which the blood flows, an elongated rotary member 5 having a pair of rollers 5a and 5b at its opposite ends, and a DC motor 6 operatively connected to the rotary member for rotating it. The tube 4 enters the housing 3 through an opening 3a formed therein, extends along the internal peripheral surface of the housing 3 by about 180 degrees, and exits from another opening 3b formed in the wall of the housing 3. And when the rotary member 5 is rotated by the motor 6, one of the rollers 5a and 5b squeezes the curved portion 4a of the tube 4 to deliver the blood residing in the tube 3. In order to obtain a pulsating flow of the blood with this roller-type pump 1, the motor 6 needs to be rotated intermittently. More specifically, the motor 6 needs to be alternately rotated and stopped at desired intervals. In this case, an amount of the blood delivered by one continuous operation or one beat of the pump 1 can be obtained by multiplying the double of the internal volume of the curved portion 4a of the tube 4 by the number of revolution of the rotary member 5 made during one continuous operation of the pump 1.

As is appreciated from the above description, in order to deliver a desired amount of the blood per a predetermined period of time at a desired beat rate, the pump 1 must be supplied with a control signal indicative of desired rotation speed of the motor 6 and proper starting and stopping timings thereof. The control unit 2 produces this signal and supplies it to the motor 6 so that the pump 1 operates at the desired speed and intervals.

The construction of the control unit 2 will now be described in more detail.

The control unit 2 comprises an R-wave detection circuit 7, a pulse generator 8, an input signal interface 9, a processing unit 10 and a gate circuit 11. The R-wave detection circuit 7 discriminates each of R waves from an electrocardiographic wave Wh supplied via a selection switch 12 from an electrocardiograph 13, and feeds a signal indicative of the timings of the detected R waves together with data representative of the intervals thereof to an input section of the processing unit 10. This detection circuit 7 is so designed that the threshold level for the discrimination of the R waves can be manually adjusted to any desired signal level. The pulse generator 8 generates pulse signals similar in timing to the electrocardiogram Wh of a patient and is used only when the electrocardiogram Wh does not have a sufficient signal level, or when the electrocardiogram is not stable. The pulse generator 8 may be so designed as to output pulses of which interval is manually adjustable to that of any R waves. The input signal interface 9 converts values or parameters set by an operator via an operator's panel 14 into the corresponding electronic data signals and supplies these data signals to the input section of the processing unit 10, the parameters including a desired flow rate of the blood (ml/min), a desired delay time (ms) to be lapsed before an actuation of the pump, a desired duration time of each continuous operation of the pump 1 expressed in percentage of the R—R interval(%), and the amount of the blood delivered by one revolution of the rotary member 5, i.e., the double of the internal volume of the curved portion 4a of the tube 4 (ml). The processing unit 10 comprises a well known microprocessor and an output circuit (a drive circuit), and is designed to calculate, from the respective data supplied from the input signal interface 9 and the detection signals of the R-wave detection circuit 7, a desired rotation speed of the motor 6 of the pump 1. And the processing unit 10 outputs from its output circuit pulse signals at intervals equal to those of the R waves, each of which pulse signals rises when the delay time has lapsed from the corresponding R wave, and maintains a signal level corresponding to the calculated rotation speed for a period identical with the duration. The gate circuit 11 transfers the pulse signals outputted from the output circuit of the processing unit 10 to the motor 6 but prohibits the pulse signals from continuing to be transferred beyond the next R wave.

Thus, when the following parameters are inputted through the operator's panel 14 to the control unit 2:
(a) R—R interval; 0.85 sec (70 beat/min)
(b) Amount of flow of the blood per one revolution of the pump (discharge of the pump); 30 ml/revolution
(c) Desired flow rate of the blood; 6000 ml/min
(d) Duration of each operation of the pump; 50%
the processing unit 10 calculates the required rotation speed of the pump 1 in the following manner:

First, the amount of the blood required to be delivered by each continuous operation or one beat of the pump 1 is calculated by a formula given below.

$$\frac{\text{desired flow rate}}{\text{beat rate}} = \frac{6000 \text{ (ml/min)}}{70 \text{ (beat/min)}} = 85 \text{ (ml/beat)}$$

The number of revolution of the pump 1 necessary to feed the above amount of the blood is then calculated by dividing the result of the above calculation by the amount of flow of the blood per one revolution of the pump.

$$\frac{85 \text{ (ml/beat)}}{30 \text{ (ml/revolution)}} = \frac{85}{30} \text{ (revolution/beat)}$$

Each period during which the pump continuously operates is 50% of the R—R interval, and therefore the required rotation speed of the pump is calculated as follows:

$$\frac{60 \text{ (sec/min)}}{0.85/2 \text{ (sec/beat)}} \times \frac{85}{30} \text{ (revolution/beat)} = 400 \text{ (rpm)}$$

The control unit 2 outputs pulses at an interval of 0.85 second each of which pulses rises 0.4 second after the corresponding R-wave and maintains a signal level corresponding to 400 rpm for a period of 0.85/2 second.

As described above, with the construction of this apparatus, the desired rotation speed of the pump 1 is automatically calculated in accordance with the inputted parameters, and the pump 1 is controlled to rotate intermittently in synchronism with the R waves at the calculated speed with the desired delay times and durations. Thus, the pump 1 can feed by its one continuous operation or one beat a pulse of flow of the blood equal in amount to that fed by one beat of the heart. And as a sufficient blood pressure can be applied to the coronary arteries by virtue of the pulsating flow of the blood, a diastolic augmentation can be attained. Further, the left ventricle may not be subjected to an abnormal load, since the blood is fed in a pulsating manner in synchronism with the beat of the heart. And therefore, with this apparatus, a complicated and long time operation can be carried out without using a ventricle-asisting system which is liable to damage the cardiac muscle. Thus, this apparatus is particularly suitable for use in such an operation that has any possibility of damaging the cardiac muscle.

Figure 3:
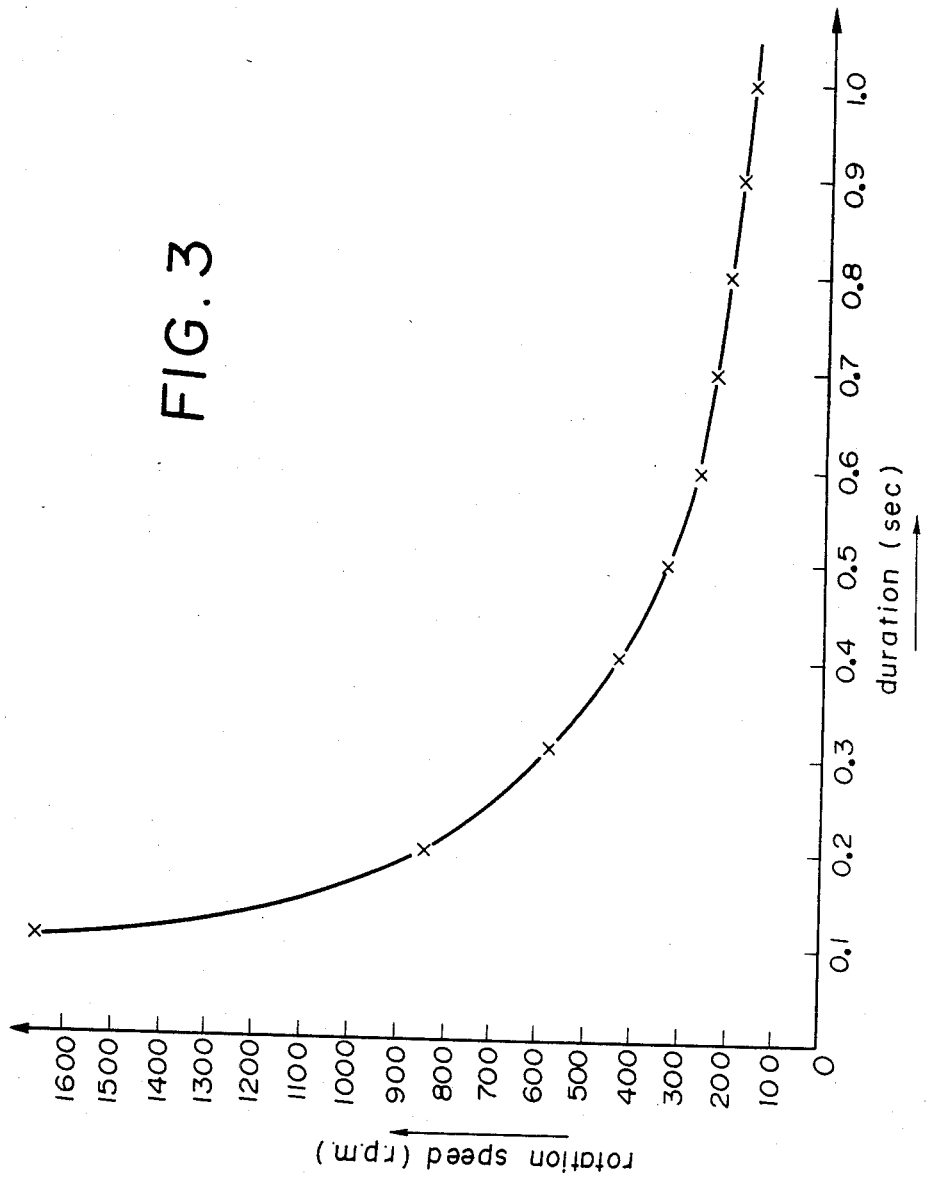
FIG. 3 is an illustration showing the relationship between rotation speed and duration of a motor of the apparatus of FIG. 2.

FIG. 3 shows the relationship between the rotation speed and the duration of each operation of the pump 1 under the following conditions:

(1) Amount of flow of the blood per one revolution of the pump 1 (discharge of the pump); 30 (ml/revolution)
(2) Beat rate; 70 (beat/min)
(3) Desired flow rate of the blood; 6000 (ml/min)

In the figure, the abscissa represents the rotation speed in rpm and the ordinate represents the duration in second.

Figure 4:
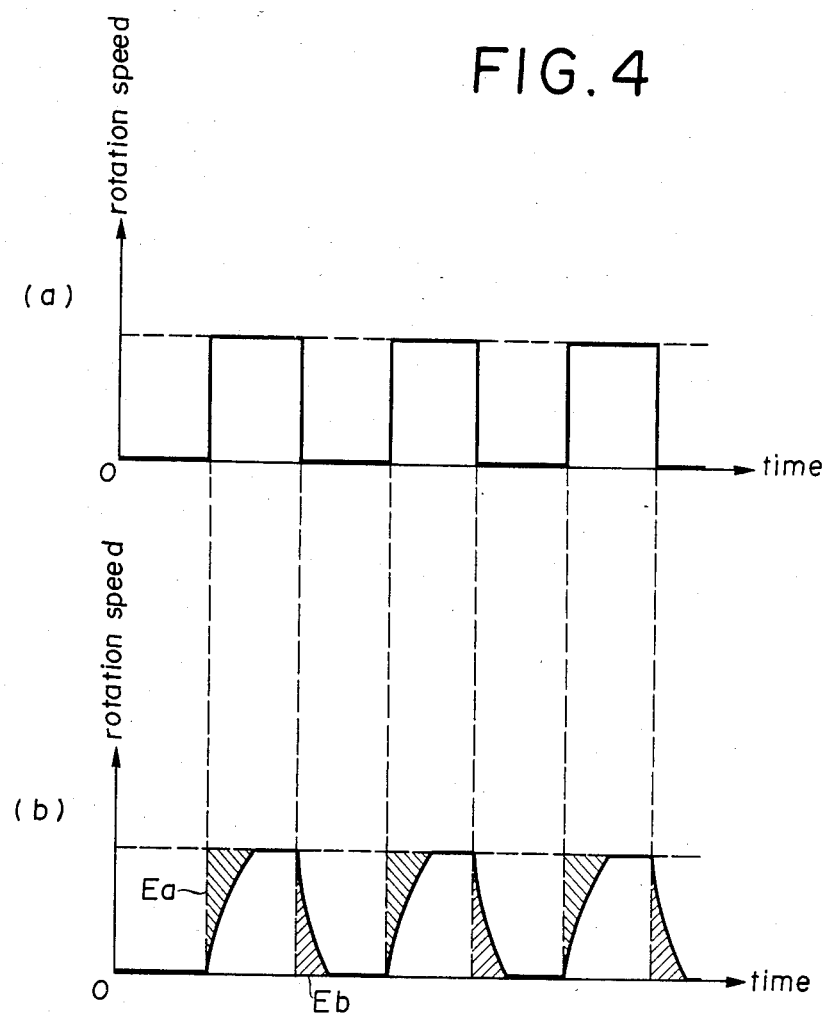
FIGS. 4-(a) and 4-(b) are illustrations showing an ideal waveform of the rotation speed of the motor and an actual waveform thereof, respectively.

FIG. 4-(a) shows an ideal waveform of the rotation speed of the pump 1, actually however, it normally takes certain periods of time to accelerate the pump 1 to a desired rotation speed and to decelerate it to zero, respectively, as shown in FIG. 4-(b). And as the acceleration characteristic or acceleration period of the pump 1 differs from the deceleration characteristic or deceleration period thereof, the error in number of revolution represented by hatched area Ea, which occurs during each of the accelerations of the pump, does not become equal to the error represented by hatched area Eb which occurs during each of the decelerations of the pump. The difference between the two errors Ea and Eb reaches to an unnegligible amount when accumulated for a long period of time. This is quite undesirable. In addition to the above problem, the actual rotation speed of the pump 1 can be deviated from the calculated rotation speed due to a drift in the circuitry of the control unit 2 and due to variation of mechanical condition of the pump 1 itself. This causes the above-described error to be further increased.

Figure 5:
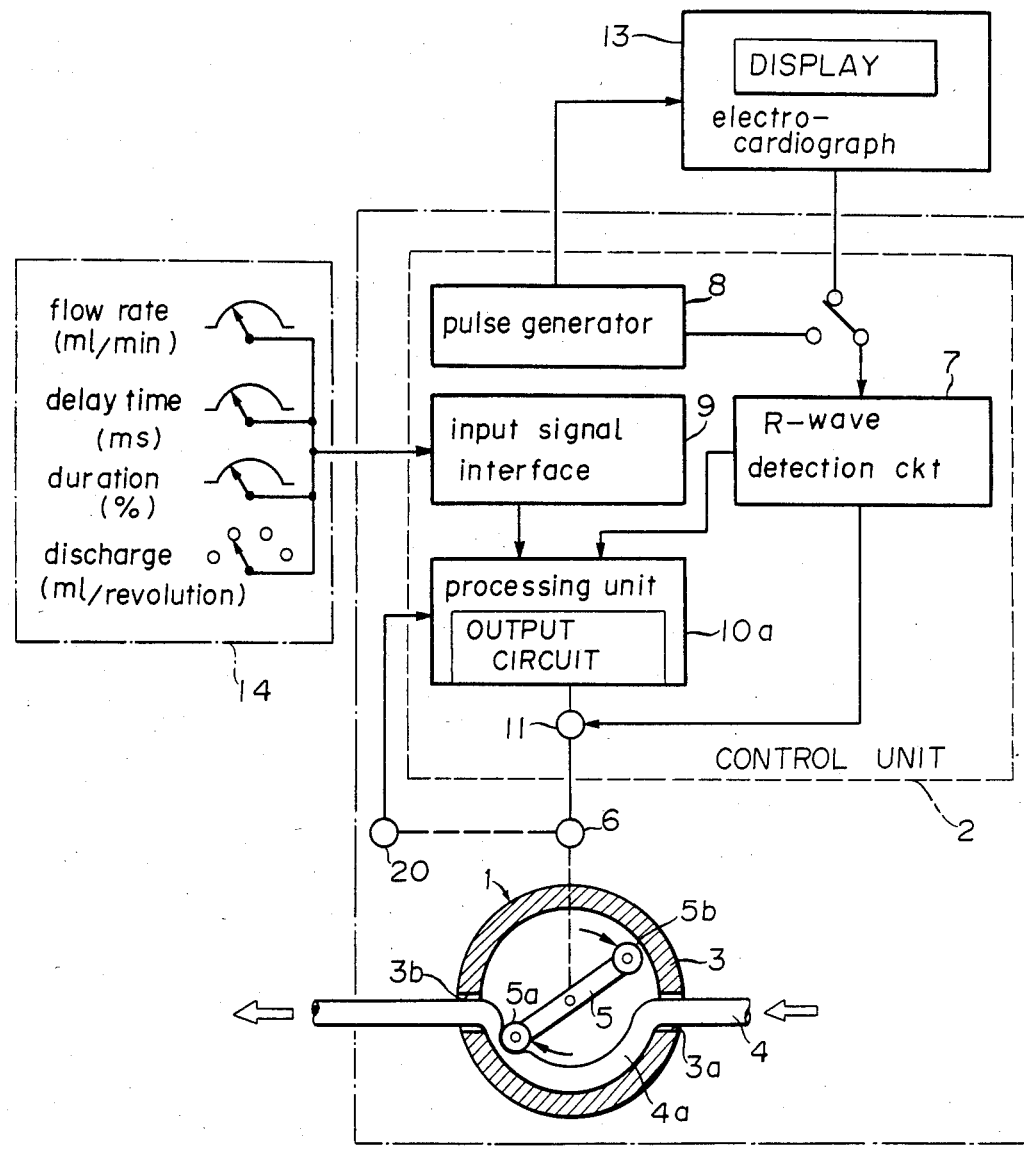
FIG. 5 is a block diagram of a modified blood pump apparatus provided in accordance with the present invention.

FIG. 5 shows another blood pump apparatus which is modified so as to solve the above problems. This modified apparatus differs from the apparatus of FIG. 2 in that a detector 20 for detecting number of revolution of the motor 6 is provided on a shaft thereof. The detector 20 comprises, for example, a rotary encoder operatively connected to the shaft of the motor 6 for outputting pulses of which number is proportional to that of revolution of the motor 6. The pulses are fed to an input section of a processing unit 10a. The processing unit 10a is almost identical with the processing unit 10 of the apparatus of FIG. 2 but includes a counter means for counting the pulses supplied from the detectors 20 and an error correction program to be executed before outputting each of the pulse signals for driving the motor 6. In this modified apparatus, threshold level L of an R-wave detection circuit 5 for discrimination of R waves is supplied to an electrocardiograph 13 so that the threshold level L can be displayed on the same display where the electrocardiogram is displayed.

Figure 6:
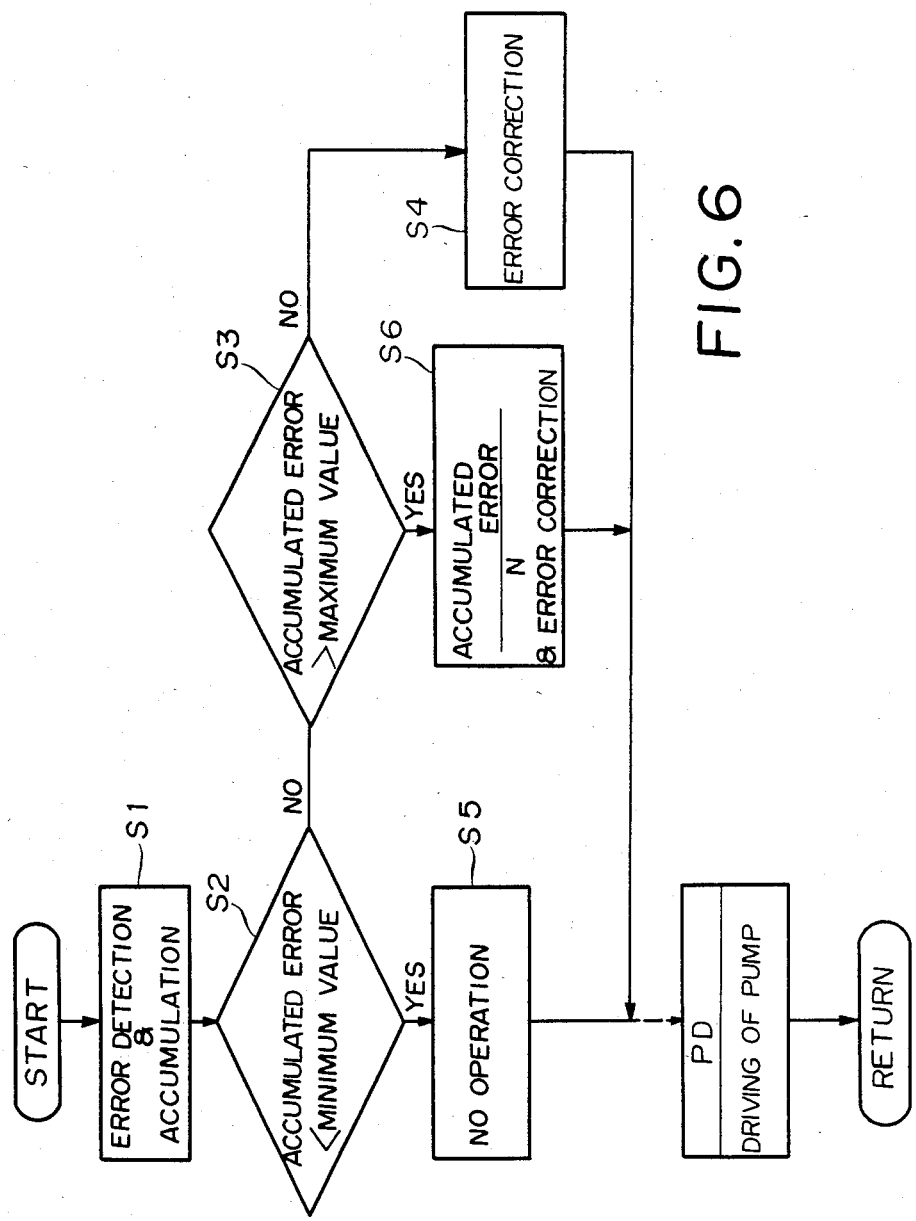
FIG. 6 is a flow chart of an error correction program executed in the apparatus of FIG. 5.

FIG. 6 shows a flow chart of the error correction program. The processing unit 10a executes this correction program immediately before executing a pump driving program PD by which one pulse signal for driving the motor 6 is generated in a manner as described for the apparatus of FIG. 2. Upon entering into this error correction program, the processing unit 10a reads contents of the counter means, which represent the actual number of revolution of the pump made during the preceding operation of the pump, and subtracts the contents of the counter means from the desired revolution number of the pump previously calculated by the processing unit. Thus the processing unit 10a obtains an error occurred during the preceding operation of the pump 1 and accumulates it in an accumulator (step S1 of FIG. 4). The processing unit 10a then determines whether the accumulated error is less than a minimum value which can be accurately compensated by this apparatus (step S2). And if the determination result is "NO", the processing unit 10a further determines whether the accumulated error is more than a maximum value which is allowable to be compensated for during one beat of the pump 1 (step S3). This determination is made to avoid an abrupt variation of flow of the blood. And this determination results is also "No", the processing unit modifies the desired rotation speed of the pump 1 previously calculated so as to compensate for the accumulated error and clears the accumulated error (step S4). In this case, the processing unit modifies the calculated desired rotation speed in accordance with the result of addition of the accumulated error and a possible error in the next operation of the pump which can be estimated from the accumulated error. For example, if it is expected that the same amount of error as the present accumulated error will occur in the next operation of the pump, the processing unit 10a modifies the desired rotation speed of the pump previously calculated by adding the double of the amount of the accumulated error thereto. Then the processing unit 10a executes the pump driving program PD with data representative of this modified rotation speed of the pump to generate a driving pulse in a manner described for the apparatus of FIG. 2.

At the step S2 of the error correction program, if it is determined that the accumulated error is less than the minimum value, the processing unit executes the pump driving program PD without modifying the desired rotation speed of the pump previously calculated (step S5).

At the step S3 of the error correction program, if it is determined that the accumulated error is more than the maximum value, the accumulated error is divided by an appropriate number N (N=1, 2, 3, ... ), and the desired rotation speed of the pump previously calculated is modified by adding the division result thereto. And at the same time the accumulated error is updated by subtracting the division result therefrom (step S6). Thus, the accumulated error excessive in amount can be distributed for compensation over the succeeding operations of the pump.

With this modified apparatus, any error in number of revolution of the pump 1 is automatically compensated and the blood can be supplied to a patient at a very accurate flow rate.

What is claimed is:

1. A blood pump apparatus for pumping blood into a body of a patient in synchronism with an output of an electrocardiograph connectable to the body of the patient comprising:
   (a) a fluid pump driven by a variable rotation speed electric motor for feeding the blood;
   (b) data input means for inputting data relating to operation of said pump, said data including data representative of discharge of said pump per a predetermined number of revolutions of said motor, data representative of delay time to be lapsed before an actuation of said motor, data representative of duration of the actuation of said motor, and data representative of amount of the blood to be fed per a unit period of time;
   (c) R-wave detection means for detecting R waves from the output of the electrocardiograph to output a signal indicative of timing of said R waves and data representative of interval between two adjacent ones of said R waves;
   (d) means for calculating, in accordance with the data representative of said discharge of the pump, said duration of the actuation of said motor, said amount of blood to be fed and said interval between the two adjacent R waves, a rotation speed of said motor required to feed said amount of blood per said unit period of time, said calculation means outputting a signal representative of said calculated rotation speed and said duration of the actuation of said motor; and
   (e) motor drive means responsive to said signal indicative of said timing of the R waves and said signal representative of said calculated rotation speed and duration of the actuation of said motor for driving said motor so that said motor begins to rotate at said calculated rotation speed when said delay time has lapsed from each of the detections of said R waves and stops when said duration has lapsed.

2. A blood pump apparatus according to claim 1 further comprising pulse generator means for generating pulse signals similar in timing to said R waves, and switch circuit means for selectively supplying one of the output of the electrocardiograph and an output of said pulse generator means to said R-wave detection means.

3. A blood pump apparatus according to claim 1 or claim 2 further comprising means for detecting number of revolution of said motor, said calculating means correcting said calculated rotation speed in accordance with an output of said number-of-revolution detecting means.

4. A blood pump apparatus according to any one of claims 1 to 3, wherein said fluid pump is a roller-type pump comprising a housing having a cylindrical chamber, a flexible tube extending along an internal surface of said chamber in a plane generally perpendicular to an axis of said chamber, and a rotary member rotatably supported within said chamber and having at least one roller mounted thereon, said roller squeezing said tube when said rotary member is rotated.

* * * * *